(12) United States Patent
Beyens et al.

(10) Patent No.: US 9,958,405 B2
(45) Date of Patent: May 1, 2018

(54) REVERSE FILLING CARBON AND TEMPERATURE DROP-IN SENSOR

(71) Applicant: Heraeus Electro-Nite International N.V., Houthalen (BE)

(72) Inventors: Dries Beyens, Kinrooi (BE); Guido Jacobus Neyens, Opoeteren (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 250 days.

(21) Appl. No.: 14/971,363

(22) Filed: Dec. 16, 2015

(65) Prior Publication Data

US 2016/0209342 A1 Jul. 21, 2016

Related U.S. Application Data

(60) Provisional application No. 62/105,889, filed on Jan. 21, 2015.

(51) Int. Cl.

| | | |
|---|---|---|
| *G01K 1/00* | (2006.01) | |
| *G01N 25/04* | (2006.01) | |
| *G01K 13/12* | (2006.01) | |
| *G01K 7/02* | (2006.01) | |
| *G01N 33/20* | (2006.01) | |
| *C21B 7/24* | (2006.01) | |

(Continued)

(52) U.S. Cl.
CPC ............... *G01N 25/04* (2013.01); *C21B 7/24* (2013.01); *C21C 5/4673* (2013.01); *F27D 21/00* (2013.01); *F27D 21/0014* (2013.01); *G01K 7/02* (2013.01); *G01K 7/025* (2013.01); *G01K 13/125* (2013.01); *G01N 1/125* (2013.01); *G01N 33/206* (2013.01)

(58) Field of Classification Search
USPC ......................................... 374/208, 163, 139
See application file for complete search history.

(56) References Cited

U.S. PATENT DOCUMENTS 3,357,598 A 12/1967 Kraft
3,374,122 A 3/1968 Cole
(Continued)

FOREIGN PATENT DOCUMENTS

CN 201041556 Y 3/2008

*Primary Examiner* — Mirellys Jagan
(74) *Attorney, Agent, or Firm* — Panitch Schwarze Belisario & Nadel LLP

(57) ABSTRACT

A drop-in probe includes a measurement head having an immersion end and an opposing second end having an end face. The measurement head is formed of first and second body halves configured to mate together along a parting line. A sample chamber, arranged within the measurement head, is thermally isolated from a cooling mass thereof and includes a metal wall having a thickness of 2.5 mm or less. An inlet tube has an inlet opening to the sample chamber. The inlet opening has a diameter $D_{inlet}$ and is spaced apart from the end face of the measurement head at a distance of at least $$\frac{D_{inlet}}{2}.$$

When the sample chamber is filled with a sample of the molten metal, a ratio of a mass of the metal sample to a mass of the metal wall of the sample chamber is greater than 2.6 and less than 6.

16 Claims, 7 Drawing Sheets

(51) Int. Cl.
*C21C 5/46* (2006.01)
*F27D 21/00* (2006.01)
*G01N 1/12* (2006.01)

(56) References Cited

U.S. PATENT DOCUMENTS

| | | | |
|---|---|---|---|
| 3,463,005 A | | 8/1969 | Hance |
| 3,559,452 A | | 2/1971 | Perbix et al. |
| 3,574,598 A | | 4/1971 | Kern et al. |
| 3,656,346 A | * | 4/1972 | Collins ............... G01N 1/125 374/140 |
| 3,748,908 A | * | 7/1973 | Falk ................... G01K 13/125 136/231 |
| 4,141,249 A | | 2/1979 | Ishikawa et al. |
| 4,842,418 A | * | 6/1989 | Conti .................. G01K 13/125 374/139 |
| 4,881,824 A | | 11/1989 | Falk et al. |
| 5,033,320 A | | 7/1991 | Baerts |
| 5,577,841 A | | 11/1996 | Wall |
| 6,142,664 A | * | 11/2000 | Ikawa ................. G01K 13/125 374/140 |
| 6,299,348 B1 | * | 10/2001 | Theuwis ............. G01K 7/025 136/226 |
| 9,116,054 B2 | | 8/2015 | Beyens |
| 2003/0193988 A1 | * | 10/2003 | Bates ................. G01N 25/4866 374/10 |
| 2012/0082183 A1 | * | 4/2012 | Beyens ............... G01K 13/125 374/179 |
| 2013/0098173 A1 | | 4/2013 | Neyens et al. |

* cited by examiner

REVERSE FILLING CARBON AND TEMPERATURE DROP-IN SENSOR

CROSS-REFERENCE TO RELATED APPLICATIONS

This application claims the benefit of U.S. Provisional Patent Application No. 62/105,889, filed Jan. 21, 2015, the entire contents of which are incorporated by reference herein.

BACKGROUND OF THE INVENTION

The present invention relates to a drop-in sensor measuring head having a forward facing bath thermocouple and a reverse-filling solidification chamber. The drop-in sensor according to the present invention allows for rapid and accurate measurements of the bath and liquidus temperatures of molten metals.

During the steelmaking process, oxygen is combined with carbon dissolved in the steel to remove the carbon, while at the same time providing heat from the combustion process. When the carbon content, as well as the molten metal temperature, are known, the furnace operator can decide the extent of additional refining or end the process. It is therefore advantageous to have available information regarding both the temperature of the liquid metal and the carbon content.

U.S. Pat. No. 3,559,452 describes the usefulness and terminology of carbon determination in molten steel during the converter process. It is a common practice to employ disposable immersion sensors, such as disclosed in U.S. Pat. No. 5,577,841, which are attached to a metal support lance and manually manipulated by an operator to obtain temperature and thermal analysis information. In many instances, ready access to the interior of steel processing vessels in order to contact the molten metal with disposable immersion measuring sensors, and thus determine the temperature and carbon content of the metal, is severely limited.

Large mechanical auxiliary lances, such as those described in U.S. Pat. No. 4,141,249, which are suitable for use in a converter process, have been constructed to immerse multifunctional sensor probes, such as those described in U.S. Patent Application Publication No. 2013/0098173, specially designed to attach to these auxiliary lances. However, there is a large capital expense required to modify an existing converter with an auxiliary lance. Once installed, the on-going maintenance of this equipment is difficult in the industrial environment of a typical steel mill increasing the cost per measurement. All of these expenses present a barrier to low cost steel production.

Drop-in or thrown-in devices have been developed to avoid the large capital investment of the auxiliary lance. Such measuring devices are dropped into the vessel from an access port well above the molten metal surface. These devices trail a signal cable that relays the thermocouple output to remote instrumentation providing data about the degree of processing accomplished, thereby enabling an operator to judge the extent of further processing required. Such devices for temperature measurement or thermal analysis are described in U.S. Pat. No. 3,357,598 and U.S. Pat. No. 3,463,005.

One difficulty in obtaining consistent and reliable molten metal sensor information from conventional drop-in devices is ensuring that the dropped sensor enters the liquid steel and remains submerged for a duration sufficient to obtain the desired measurements. Specifically, during the refining process, a large amount of slag floats on top of the molten steel and impedes the penetration of the dropped device through the slag layer and into the molten metal. If the displaced volume of the molten steel is significantly greater than the weight of the portion of the drop-in sensor designed to be immersed therein, the sensor will float rather than become immersed. The buoyant force acting on the body immersed in the molten steel will act in an upward direction, thereby resulting in a floating position partially or totally above the liquid steel.

It has been traditionally recognized that the random drop of these sensors could, in some circumstances, result in errors when the thermocouple or an opening to a thermal arrest chamber is not orientated for optimal contact with the molten steel. Both a side-extending thermocouple, such as disclosed in U.S. Pat. No. 3,574,598, or a side-opening thermal arrest chamber, such as disclosed in U.S. Pat. No. 3,463,005, could face away from the metal and thus experience errors due to limited molten metal contact, partial filling or not being filled at all as a result of floatation.

In CN 201041556, the opening to the thermal arrest chamber is positioned opposite the immersion end. The chamber is constructed of resin sand and is specified to be axially located. Since it has the liquid metal of the solidification chamber on its inner walls and its outer wall is directly exposed to the molten bath, it will have inefficient thermal capacity to chill the metal that has entered the inlet. Without complete thermal isolation of the solidification chamber, the molten metal bath can act as a heat pump, thereby heating the liquid phase of the solidifying mass in the chamber and resulting in liquidus measurement errors. These errors increase in number and magnitude as the molten metal superheat increases. In the conventional sense, superheat is determined by the difference of the temperature of the molten metal at the time of sampling over the temperature detected at the onset of its solidification. When a portion of the chamber exists outside of the main measuring head and is in thermal communication with the bath, it is subject to direct heating from the pool of molten metal which greatly diminishes the cooling ability of the chamber materials. The exit of the cable is secured to the metal head by a metal ring, but is not restricted in its lateral movements, which could destroy the resin sand solidification chamber in certain orientations.

To overcome this problem, improvements in these devices typically relied upon the bulk density of the device in relation to that of the liquid slag and that of the liquid steel, so as to aid in the descent of the device through the slag and into the steel, while providing some orientation toward the desired immersion direction. Bulk density is used herein to mean the overall density, including the sensor components and any voids within the overall immersed device and signal cable according to it submersed length. The multiple cross-sections in each configuration shown in U.S. Pat. No. 9,116,054 are graduated to accomplish a preferred orientation. That is, the total bulk density can be less than 7 g/cm$^3$ as long as the a dense section of the measuring head has an apparent density greater than 7 g/cm$^3$ necessary to ensure immersion of the measuring elements. Since liquid steel is approximately 90 percent as dense as solid steel, massive void free sections forward of the sensing elements are required to provide this orientation. The measuring elements are thus positioned at a distance removed from the forward face of the sensor. However, a sensing element at the forward face is the exact location that is favored for the longest exposure to the steel to be measured.

Still, at times, when the orientation is correct, that is, placing the temperature sensor in the metal and with a thermal arrest chamber that has filled with liquid metal, there exists a potential that accurate and reliable measurements are not obtained. U.S. Pat. No. 5,033,320 describes the necessary relation of the mass of the cooling chamber to the rate of solidification to obtain accurate thermal arrest information. While the bath temperature can be detected in a relatively short time, a longer time is required for the solidifying metal to reach a stable thermal balance between the released latent heat of fusion and the heat extraction of the cooling mass, and thus to obtain a liquidus plateau. From the time the drop in sensor is released, the trailing signal cable is constantly combusting. There is a potential for the destruction of the trailing signal cable to advance to a failed state before obtaining a longer duration liquidus plateau, such as that experienced for a high bath temperature, and thus failing to obtain the desired measurement. This is not new to the art. Various isolative and protective strategies have been employed in prior devices to delay the destruction of the signal cable by surrounding a portion of the signal cable exiting the measuring head with tubes of refractory material or cardboard, such as in U.S. Pat. No. 3,374,122.

Although this delay is temporary, it is suggested by U.S. Pat. No. 4,881,824 that when the measurement head has an adjustable paperboard tube float on its end facing away from the immersion end and the signal cable is guided through this tube, such an arrangement provides for sufficient protection of the signal cable to obtain the desired measurements. At the same time, the low density material also serves as a counterbalance, orientating the measuring head and stabilizing it in a down-facing position. Specifically, the temperature and sampling device of U.S. Pat. No. 4,881,824 does not have a solidification chamber but shows an "extension". From the specification of U.S. Pat. No. 4,881,824, the low density float is adjustable along the length of the pipe to ensure that the proper immersion depth will be obtained with the sensor, and the float will maintain the probe in a generally erect position to avoid having the lead wires touch the surface of the molten metal which can damage the wires. The float keeps the pipe from tipping. As soon as the float encounters the melt or slag, it will tend to "right" the pipe. During immersion, the fusible link will melt and release the pod which will float up to the surface with the wire, allowing for retrieval of the sample mold.

However, in practice, the slag volume varies from heat to heat and during the steelmaking process, thereby eliminating any advantages or reason to have adjustable floats. This extension is not for the purpose of venting the measuring head. A separate hose is the vent for the sampler and is designed to separate from the measuring head. A simple comparison of the drawing of U.S. Pat. No. 4,881,824 (there are no dimensions in the specification) shows that metal parts are thicker than the float. Even if the float were weightless, the combination would not be less than the density of the slag whose value is underestimated in the specification. The metal parts have more volume than the measuring head by comparison.

Although the float should orient the measuring device in a sensor element downward position while providing protection for the trailing signals cable, this is only true in a mono-density fluid. In the typical steel making vessel with about 15% iron oxide contained in the slag at an intermediate process step, the density will be approximately 3 g/cm$^3$, whereas the steel will have a density of nearly 7 g/cm$^3$. Float-equipped devices have a forward bulk density that is still less than the liquid steel yet greater than the slag. Buoyant material attached to the opposite immersion end should orient the sensor within the first less dense liquid layer, but no quantity of float will force a lower density measuring head to submerse itself below the second higher density liquid.

It has been found that the falling momentum of the dropped sensor is paramount to positioning the measuring elements within the steel and filling the carbon chamber. Once the carbon chamber is filled, one must rely on this in-situ density, that is the measuring head density which includes a filled solidification chamber, to retard the sensor floatation for a time suitable to determine the bath temperature. A properly filled solidification chamber can deliver a correct liquidus measurement, even when partially submerged in the liquid metal.

Incremental improvements to drop-in measuring probes have eliminated many expected failure modes. However, many of these techniques are suitable only for drop-in devices utilized at the end of the converter process. This teaching is misleading. A measurement of the temperature and carbon content is most desired subsequent to the end of the process, namely during the blowing process. It is at this time that adjustments to the process could be effected. There are numerous conditions at an intermediate measurement time, that is during blowing, which escalate the difficultly of a drop-in sensor penetrating and passing into the metal at a suitable depth in order to acquire reliable measurements. With the exception of the few previously mentioned devices, most of the known prior art is absent of improvements which address the difficultly of using drop-in sensors for "in-blow" measurements.

Toward the end of decarburization, the amount of iron oxide transferred to the slag increases and thus reduces the viscosity, allowing for less drag, a reduction in slag volume due to the release of emulsified gases, and a leveling of the liquids at the end of blowing. All of these benefits are not available to those sensors dropped at in-blow. A large volume of slag that the sensor must pass through and a more viscous slag delay the exposure of the thermocouple to the steel and delay the opening of the solidification chamber. Previously employed floats can impede that passage of the measuring head through the slag. Delays in passing through the slag promotes freezing of the slag to the sensor's metal components, and thus increases the apparent volume and reduces bulk density. This, and the turbulence of the metal surface which is greatly increased during the blow, will reduce upright stability, with or without counterbalancing floats. Retention of the desired submerged position is highly compromised.

An objective of the present invention is to provide a cost efficient drop-in sensor for use in a steelmaking vessel during and prior to the end of the blowing process for providing a bath temperature and a thermal arrest temperature. More particularly, in order to correct the deficiencies of prior art devices and extend the usefulness of drop-in sensors to "in-blow" measurements, the present invention utilizes a simple construction to maximize the overall measuring head density. The measuring head according to the present invention also includes a solidification chamber which is thermally isolated from both the molten bath and the mass of the measuring head, thereby resulting in an improved ratio of cooling mass to sampled mass and thus promoting a reduction of the time to achieve a stable liquidus plateau. All external surfaces of the measurement head are designed to maximize the falling momentum and all internal spaces are maximized to minimize the buoyant tendency of the measurement head once submersed. The measurement head of the present invention also does not utilize a float.

BRIEF SUMMARY OF THE INVENTION

A drop-in probe for determining phase changes by thermal analysis of a sample of a molten metal includes a measurement head, a sample chamber arranged within the measurement head, and an inlet tube having an inlet opening to the sample chamber. The measurement head includes a first end which is an immersion end and an opposing second end having an end face. A body of the measurement head is formed of a first body half and a second body half configured to mate with the first body half along a parting line. The sample chamber is thermally isolated from a cooling mass of the measurement head, and includes a first thermocouple having a first hot junction enclosed within a metal wall. The metal wall has a thickness of 2.5 mm or less. The inlet opening has a diameter $D_{inlet}$ and is spaced apart from the end face of the second end of the measurement head at a distance of at least $$\frac{D_{inlet}}{2}.$$

When the sample chamber is filled with a sample of the molten metal, a ratio of a mass of the metal accommodated in the sample chamber to a mass of the metal wall of the sample chamber is greater than 2.6 and less than 6.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 3:
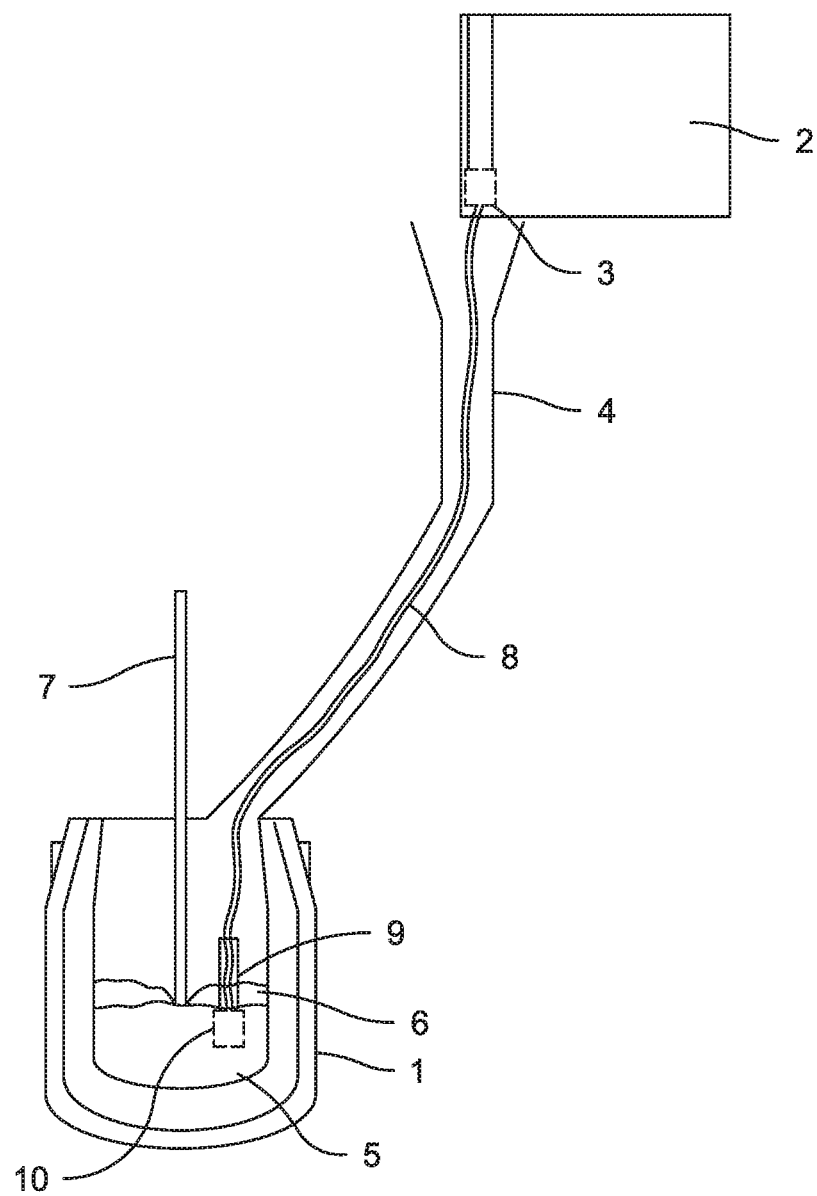
FIG. 3 is an overall schematic showing the application of a measurement device according to an embodiment of the present invention.

The present invention relates to a drop-in probe 3 for determining phase changes by thermal analysis of a sample obtained from a molten steel bath. In use, as shown in FIG. 3, a drop device 2 is arranged a few meters above a converter 1 containing molten steel 5. The drop device 2 is a hopper type device that stores drop-in probes 3 therein and can dispense a probe 3 at the appropriate time. In use, the drop-in probes 3 are automatically released from storage and fall through a guide 4 into a metallurgical melting vessel, such as the converter 1. The drop-in probe 3, and more particularly a measurement head 10 of the drop-in probe 3, plunges into the molten steel 5 after passing through and penetrating a slag layer 6 lying above the molten steel 5. Referring to FIG. 3, oxygen is preferably blown into the molten steel 5 through a blowing lance 7. The drop-in probe 3 is connected to a signal cable 8 by which measurement signals can be led to suitable instrumentation, not shown. In use, the signal cable 8 remains attached to the dispenser 2 and instrumentation.

Figure 1:
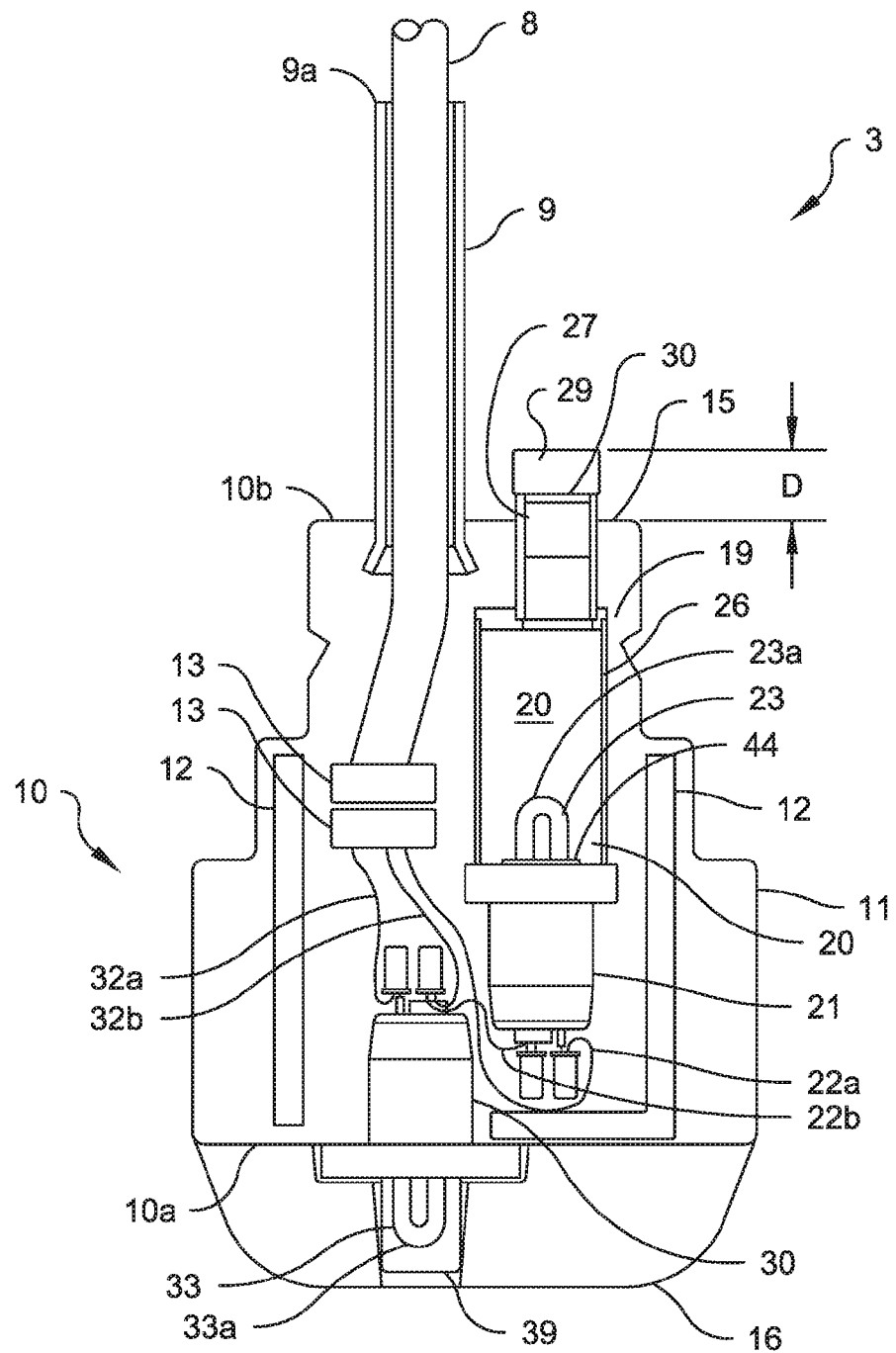
FIG. 1 is a front elevational view of one half of the measurement head according to an embodiment of the present invention.
Figure 2:
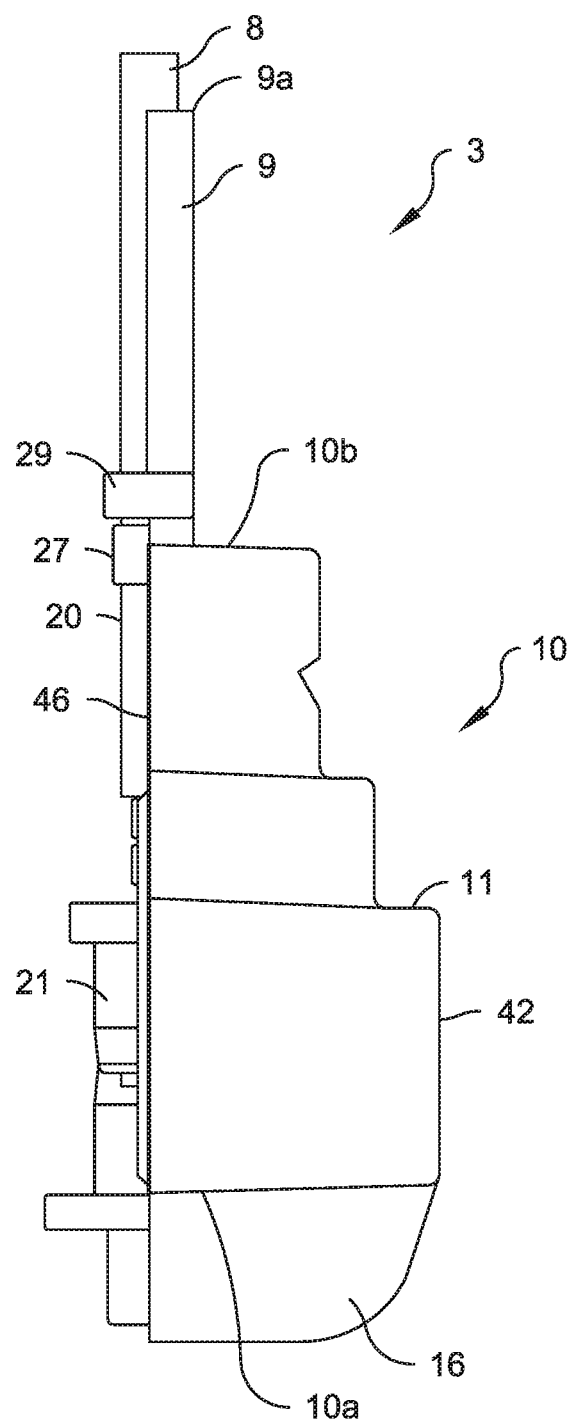
FIG. 2 is a side elevational view of the one half of the measurement head shown in FIG. 1.
Figure 2A:
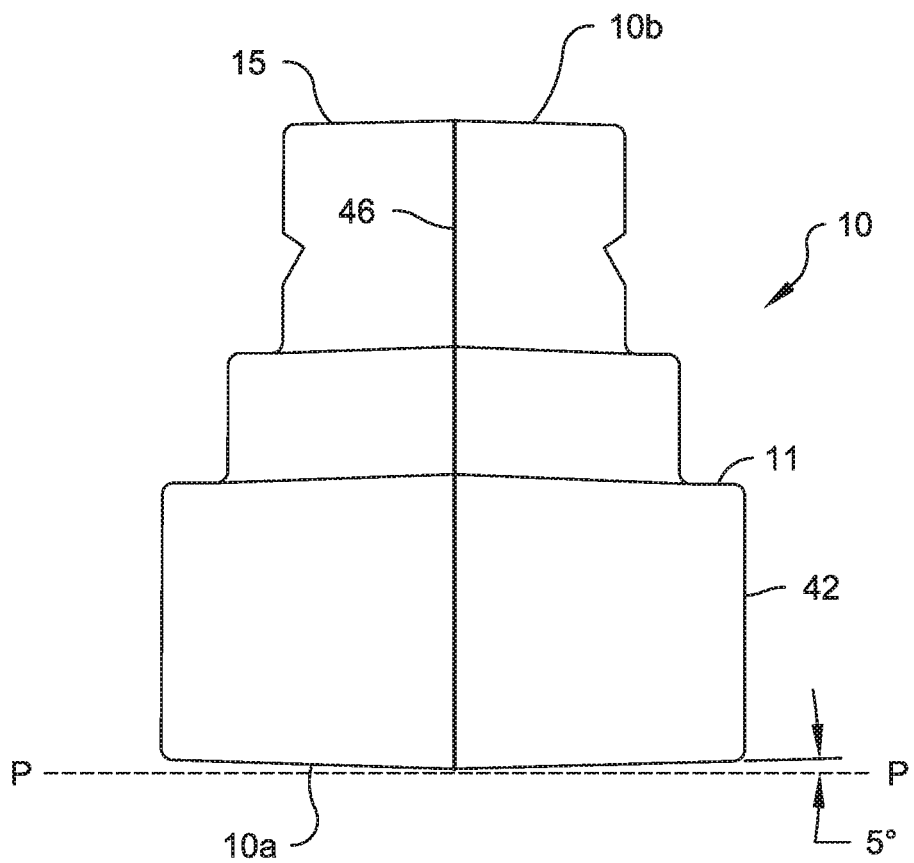
FIG. 2A is a front elevational view of the measurement head according to an embodiment of the present invention.

In one embodiment, as shown in FIG. 1, the present invention relates to a measurement device, and more particularly a drop-in probe 3, having a measurement head 10 comprising at least two parts or mating halves 11 and an extension tube 9. More particularly, a body of the measurement head 10 includes a first body half 11 and a second body half 11 configured to mate with the first body half along a parting line 46 (see FIG. 2). In a mated or assembled configuration of the measurement head 10, the first and second halves 11 are joined such that their lateral axes are angled away from the parting line 46 and the extension tube 9 of the measurement head 10. As such, in the assembled configuration, the exterior 42 of the measurement head 10 has a tapered shape relative to the parting line 46, such that there is a draft (preferably approximately 5°) from the parting line 46 of the measurement head 10 to the exterior surface 42 of the measurement head 10. More particularly, at the first end (i.e., immersion end) 10a of the measurement head 10, the exterior surface 42 is angled approximately 5° relative to a horizontal plane P of the measurement head 10 (see FIG. 2A) The position of the two halves relative to each other are fixed by the use of at least one raised ridge 12 provided on one of the first and second halves that fits into at least one corresponding depression formed in an opposite side of the other of the first and second halves 11. Preferably, a simple adhesive binds the two halves 11 together, although it will be understood that other fastening mechanisms, such as clamps, screws, rings and the like, may alternatively or additionally be employed. Preferably, the two halves 11 are made from cast iron.

The measurement head 10 preferably includes the first end 10a which is an immersion end and an opposing second end 10b having an end face or surface 15. A cushion cap 16, preferably made of a high density polymer, is preferably attached to the immersion face or end 10a. The extension tube 9 emerges from the measurement head at the end face 15, opposite the immersion end 10a, and the signal cable 8 is guided through the extension tube 9 and exits therefrom at an outlet opening 9a. The extension tube 9 protects the signal cable 8 from early damage due to the slag 6 or the molten steel 5. The signal cable 8 is preferably held within the assembled measurement head 10 by at least one compression clamp 13. The extension tube 9 may be made of a metal, such as steel, or of a plastic, a rubber, a paper material or a woven material. Preferably, the extension tube 9 is made of a metal. The extension tube 9 may be stiff or flexible.

Figure 4:
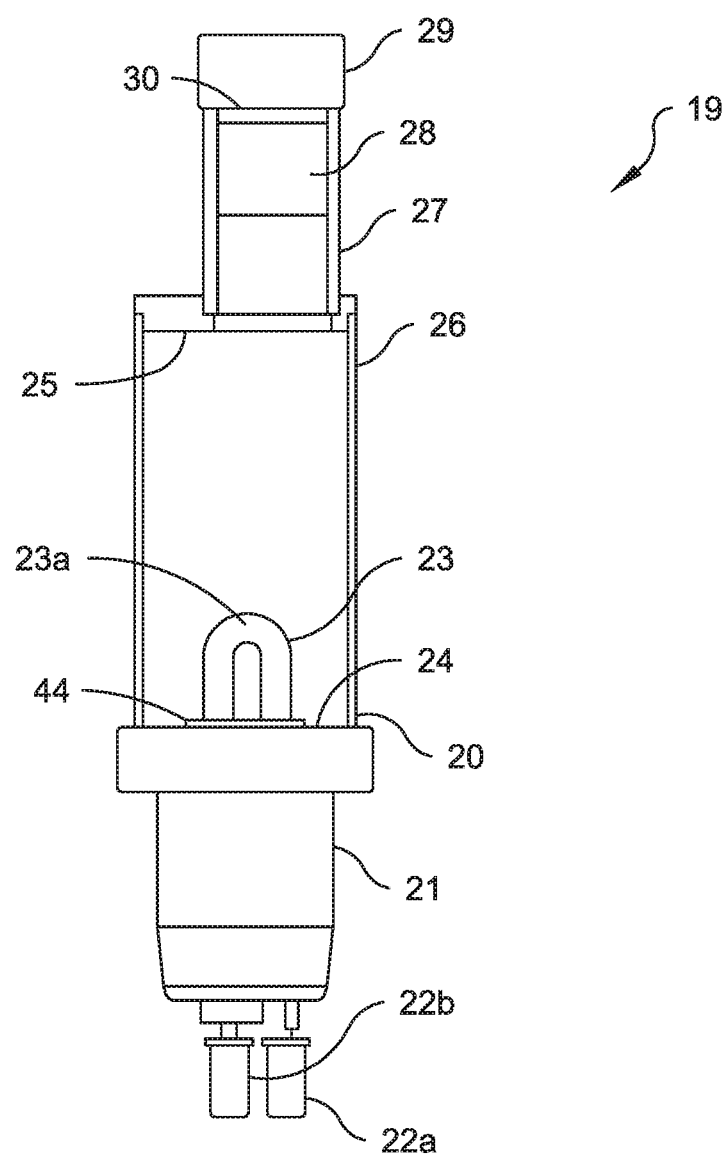
FIG. 4 is a front elevational view of the solidification chamber assembly of the measurement head according to an embodiment of the present invention.

Assembled within the measurement head 10 is a solidification or sample chamber assembly 19, as shown in FIGS. 1 and 4, including a solidification or sample chamber 20. The sample chamber 20 is a thermal arrest sample chamber (i.e., the sample chamber 20 is thermally isolated from the mass of the measurement head 10) and is preferably arranged opposite the immersion end 10a of the measurement head 10. In order to thermally isolate the sample chamber 20 from the cooling mass of the measurement head 10, the chamber 20 comprises a separate metal chamber wall 26, and more preferably a tubular metal wall 26, independent of the measurement head 10, which encloses a first thermocouple 23 positioned to measure the solidification temperature of the molten metal sample. More particularly, a first hot junction 23a of the first thermocouple element 23 projects into an interior of the sample chamber 20 and is enclosed within the metal wall 26 of the sample chamber 20. Preferably, the wall 26 has a maximum thickness of 2.5 mm.

The sample chamber 20 preferably has a floor 24, a ceiling 25, a chamber thermo-element housing 21 situated below the floor 24, and a washer 44 positioned on the floor 24. The chamber thermo-element housing 21 and the washer 44 support the first thermocouple element 23. The floor 24, the ceiling 25, and/or the chamber thermo-element housing 21 are preferably constructed of a low density material, such as resin sand, refractory cement, ceramic or similar materials known in the art.

The measurement head 10 preferably further includes an inlet tube 27. More preferably, the inlet tube 27 is a component of the sample chamber assembly 19. The inlet tube 27 preferably extends from and is supported by a surface of the ceiling 25 of the sample chamber 20 and is in communication with an interior of the sample chamber 20. A distal end of the inlet tube 27 is formed as an inlet opening 30 through which molten metal may enter and be received in the inlet tube 27 and the sample chamber 20. The inlet tube 27 is preferably made of quartz and is preferably provided with an inlet cap 29 covering the inlet opening 30. The inlet cap 29 is preferably made of steel.

The inlet tube 27 is preferably also thermally isolated from the measurement head 10. Preferably, the inlet opening 30 is spaced apart from the end face 15 of the second end 10b of the measurement head 10. More preferably, a distance D between the end face 15 of the second end 10b of the measurement head 10 and the inlet opening 28 is at least $$\frac{D_{inlet}}{2},$$

wherein $D_{inlet}$ represents a diameter of the inlet opening 30. In one embodiment, the inlet diameter $D_{inlet}$ is preferably 15 mm or less, such that the minimum separation distance D between the inlet opening 30 and the measurement head 10 is 7.5 mm or less. Such a distance between the inlet opening 30 and the measurement head 10 avoids chilling of the molten metal prior to entering the sample chamber 20. In one embodiment, a deoxidant 28 is positioned within the inlet tube 27. Preferably, the deoxidant 28 is an aluminum deoxidant, but other deoxidants known in the art may be employed.

The internal volume of the sample chamber 20 is defined as the volume contained within the chamber 20. More particularly, the volume of the sample chamber 20 is defined by the chamber wall 26, the floor 24, and the ceiling 25 of the chamber 20. The mass of metal contained in the chamber 20 can thus be calculated by multiplying the volume of the chamber 20 by the density of the metal filling the chamber 20. For the purpose of this calculation, the volume occupied by the thermocouple element 23 itself is preferably discounted from calculation of the volume of the sample chamber 20. Preferably, when the sample chamber 20 is filled with a sample of molten metal, a mass ratio is defined as a ratio between the mass of the metal accommodated in the sample chamber 20 and the mass of the metal wall 26 of the chamber 20. Preferably, the mass ratio is greater than 2.6 and less than 6

$$\left(\text{e.g.,} \; 6 > \frac{M_{sample}}{M_{wall}} > 2.6\right).$$

On one end of the measurement head 10, and more particularly at the immersion end 10a, is an additional or second thermocouple 33 with a second hot junction 33a positioned to measure the bath temperature and covered by a steel cap 39. The signal cable 8, containing electrical conductors or lead wires, extends from the measurement head 10 to instrumentation to relay the output of first, solidification thermocouple element 23 (namely along lead wires 22a and 22b) and the output of the second thermocouple element 33 (namely along lead wires 32a and 32b). The instrumentation, in turn, may display the bath temperature and solidification temperature, and hence the carbon content of the molten metal. The signal cable 8 conductors may be single paired conductors or may have a contain common conductor. The signal cable 8, the outputs, the receiving connectors and the instrumentation are known in the art.

During immersion of the measurement head 10 in molten metal, the protective caps 29, 16, 39 are melted, thereby exposing the thermocouple element 33 to the molten metal and exposing the inlet opening 30 to the inlet tube 27 to the solidification chamber 20. A thermal arrest temperature is obtained from the solidifying metal mass sampled from the liquid bath, contained within the solidification chamber 20, and is used to calculate the carbon content of the liquid metal. The inlet opening 30 to the solidification chamber 20 is positioned opposite the immersion direction (i.e., the immersion end 10a) while the bath thermocouple 33 faces the immersion direction (i.e., the immersion end 10a). After the results are obtained, the signal cable 8 is released from the dispenser device 2 and the entire drop-in probe device 3 is consumed by the liquid metal.

Another aspect of the present invention is that both the bath thermocouple 33 housing and the solidification chamber 20 are located within the two-part measurement head 10, which is separated along its longitudinal axis such that when the two parts 11 are mated, all of the internal components are fixed in place without the need for adhesives, thereby resulting in an inexpensive manner in which to assemble the device 3. Specifically, the solidification or sample chamber assembly 19 comprising the solidification/sample chamber 20, the solidification thermocouple element 23, the chamber wall 26, the ceiling 25, the floor 24 and the inlet tube 27, is placed, preferably without adhesives, within the measurement head 10, as shown in FIG. 1. Preferably, as constructed, all components of the sample chamber assembly 19 can be located within the two-part measurement head 10 with minimal empty space (i.e., voids) between the solidification chamber assembly 19 components and the walls of the measurement head 10, while still ensuring thermal isolation of the sample chamber 20 from the cooling mass of the measurement head 10 due to separation of the sample chamber 20 and the remainder of the measurement head 10. Accordingly, back filling or space occupying materials to occupy voids and to maximize apparent density, as utilized in conventional devices, are not needed, thus greatly improving the economy of assembly.

In another aspect of the present invention, the solidification chamber 20 is adaptively assembled of the thermocouple element 23 forming the floor 24 of the chamber 20, a separate metal chamber wall 26 and a ceiling component 25 supporting the metal inflow member (i.e., the inlet tube 27). The mass of the chamber wall 26 can be selected by varying its wall thickness in a sectional manner or uniformly. As such, both the cooling capacity of the chamber wall 26 and the volume of the chamber 20 can be adjusted to accommodate different blowing practices employed for the manufacture of different chemical grades of steel encountered in the steel industry, while also maintaining a target mass ratio of the cooling ability and the mass of the metal sampled. Maintaining a target mass ratio and thermal isolation for the measurement head 10 provides increased accuracy due to a stable and lengthy thermal arrest temperature obtained in a minimum amount of time at a wide range of superheats. Optimization of the solidification chamber 20 is now possible without retooling or multiple configurations of the measurement head, thereby adding to the economy of construction.

Figure 5:
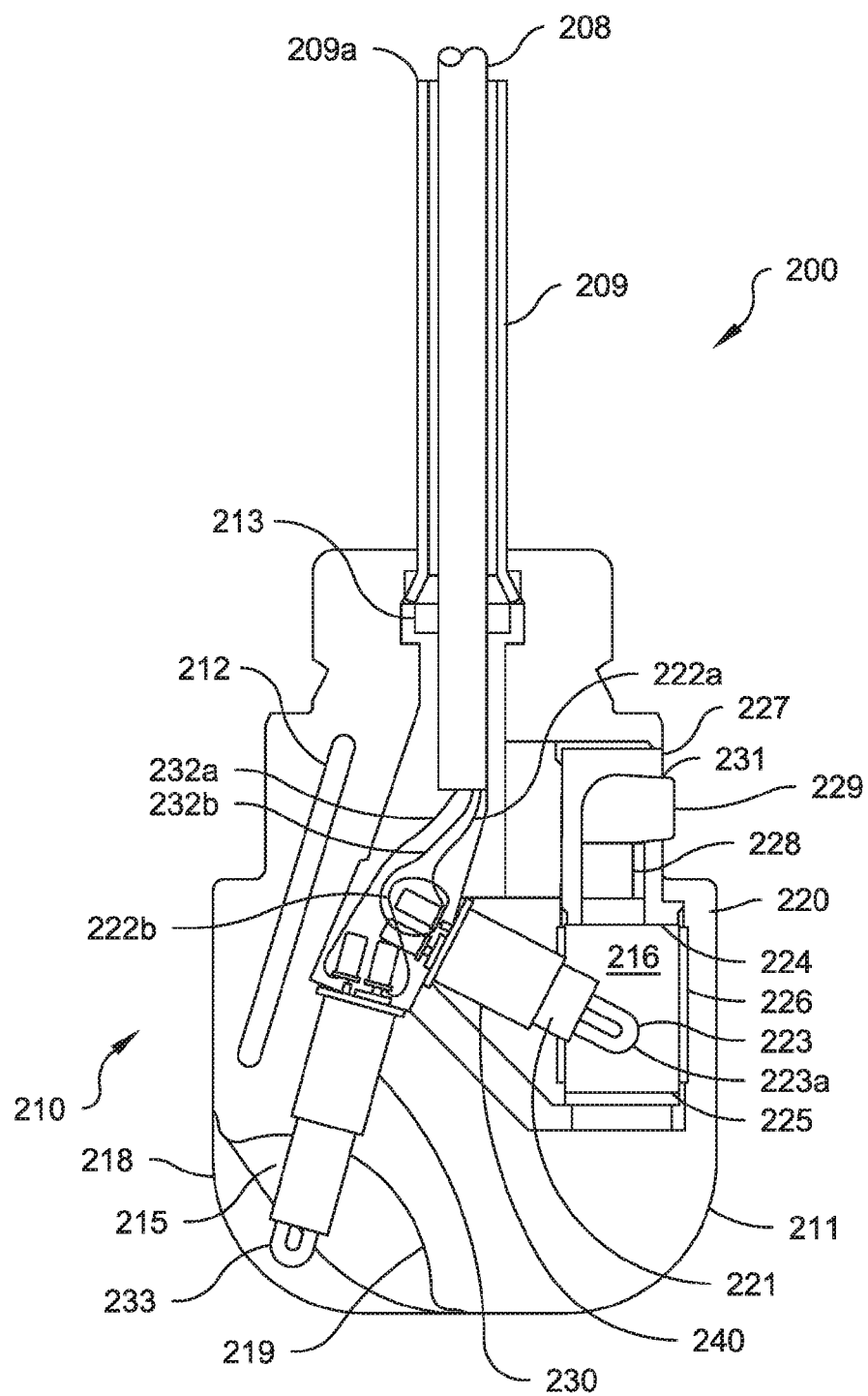
FIG. 5 is a front elevational view of one half of the measurement head according to a second embodiment of the present invention.
Figure 6:
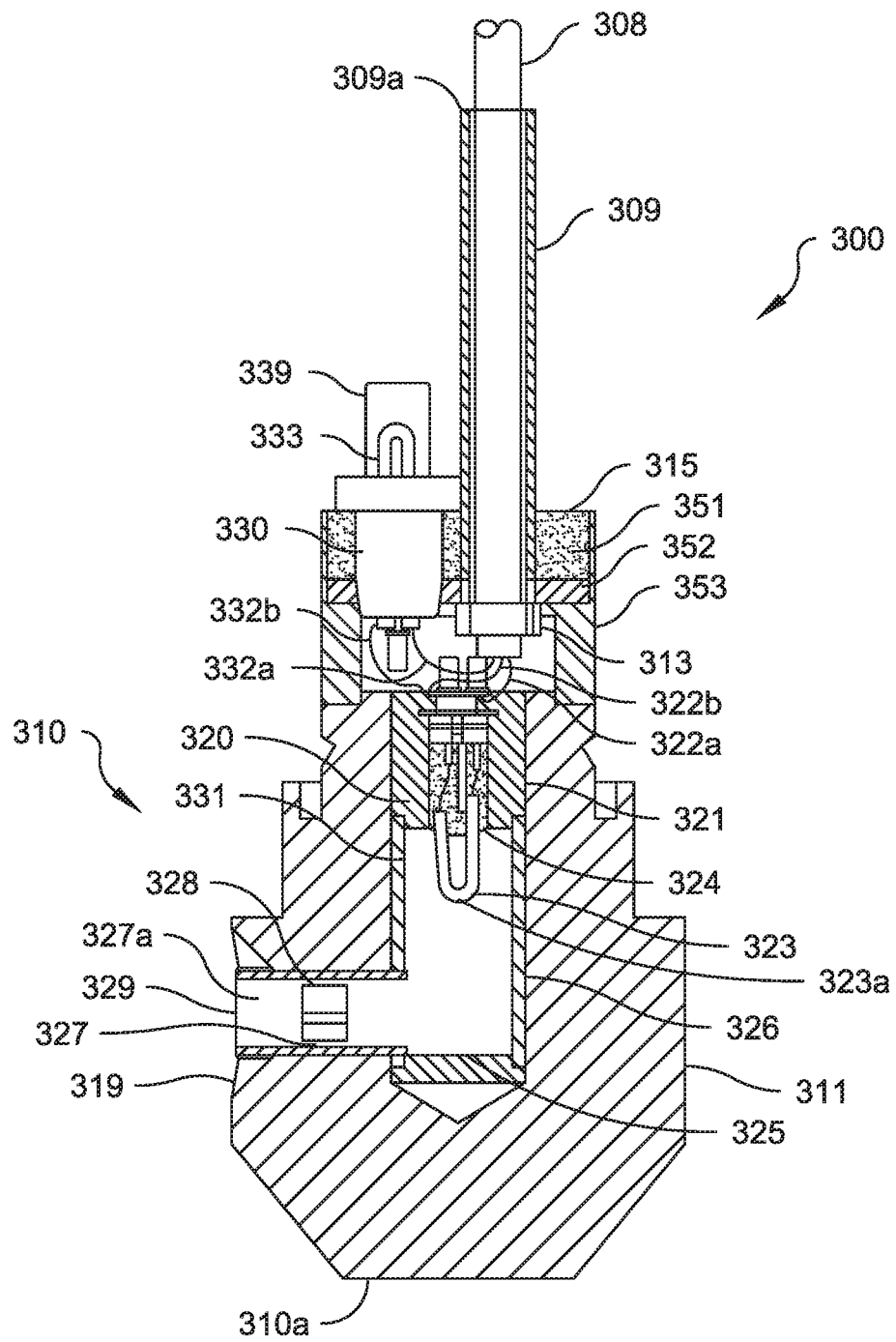
FIG. 6 is a front cross-sectional view of one half of the measurement head according to a third embodiment of the present invention.

In another embodiment, shown in FIG. 5, the drop-in sensor 200 comprises a two-part mating metal housing 211 (with the other mating half not shown). Each mating half 211 has a contour 219 removed from a respective side of the mated pair of halves 11, thereby creating a reservoir 215 for the bath thermocouple 233. Lead wires from the measuring thermo-elements are electrically connected to a signal cable 208, which exits an extension tube 209 at an outlet opening 209a. Cable clamp 213 abuts a flared end of the extension tube 209 which, in turn, is held within a cavity of the mated or assembled measurement head 210.

The reservoir 215 is preferably covered by a metal cap 218. The solidification chamber 216 is filled from a side opening 231 formed by an inlet part 227. The inlet part 227 is preferably made from a resin sand, preferably contains a deoxidant 228, and is preferably closed by a steel cap 229. The steel cap 229 may or may not be covered by a small paper disc (not shown). The minimum distance of the outermost portion of the inlet opening 231 to an adjacent metal portion of measurement head 210 is preferably greater than one half of the diameter of the inlet opening 231. A chamber thermo-element assembly 240, including the sample chamber 216 and a chamber housing 221 supporting another thermocouple element 223, is arranged with the measurement head 210. The chamber housing 221, a ceiling 224 of the sample chamber 216, and a floor 225 of the sample chamber 216 are preferably constructed of a low density material, such as resin sand, refractory cement, ceramic or similar materials known in the art. The thermocouple element 223, having lead wires 222a and 222b, has a hot junction 223a which extends into the sample chamber 216 from an opening in the generally cylindrical steel chamber wall 226.

The internal volume of the solidification chamber 216 is defined as the volume contained within the chamber 216, between the chamber wall 226, the floor 225, and the ceiling 224 of the chamber 216. The mass of metal contained in the chamber 216 can be calculated by multiplying the chamber 216 volume by the density of the metal filling the chamber 216, less the volume displaced by the extending thermocouple element 223 and the housing 221. Preferably, the mass ratio between the volume of the metal sampled and the mass of the chamber wall 226 is greater than 2.6 and less than 6

$$\left(\text{e.g.,}\ 6 > \frac{M_{sample}}{M_{wall}} > 2.6\right).$$

The solidification chamber assembly 220, comprising sample chamber 216, the thermocouple element 226, the chamber wall 226, the ceiling 224, the floor 225 and the inlet component 227 are placed without adhesives within the measurement head 210. As constructed, all components may be located within the two-part measurement head 210 with minimal empty space (i.e., voids) between the solidification chamber assembly 220 component and the walls of the measurement head 210, while still ensuring thermal isolation of the sample chamber 216 from the cooling mass of the measurement head 210. Accordingly, back filling or space occupying materials to occupy voids and to maximize apparent density, as utilized in conventional devices, are not needed, thus greatly improving the economy of assembly.

In another embodiment of the present invention, shown in FIG. 4, a measurement head 300 comprises two metal components 311 and 353, which are together mated in the longitudinal direction, and a fixation plate 352. The two metal components 311, 353 are preferably made of cast iron, but may alternatively be made from or a combination of cast iron and steel. The circular fixation plate 352, preferably made of metal, is press fit within the cylinder component 353, and thus forms a cavity for a thermo-element assembly 330. It will be understood that other attachment mechanisms, such as adhesives, fasteners and the like may be employed to secure the fixation plate 352 within the cylinder component 353. An extension tube 309, preferably made of steel, is fixed to the plate 352. A signal cable 308 extends through the extension tube 309 and exits therefrom at an outermost outlet 309a. The signal cable 308 relays outputs from thermo-element lead wires 332a, 332b, 322a and 322b to remote instrumentation and is retained within the cylindrical component 353 by a cable clamp 313. Thermo-element 333, which is covered by a steel cap 339 and supported by a thermo-element assembly 330, is positioned on the end face 315 of an end of the measurement head 310 which is opposite the immersion end 310a of the measurement head 310 and which is potted by a material 351. The potting material 351 is preferably resin sand, but may be a cement type material.

A solidification chamber assembly 320, including a solidification or sample chamber 331, is arranged within measurement head portion 311. A thermo-element 323, and more particularly a hot junction 323a of a thermocouple element 323, extends into the chamber 331 and is supported by a chamber housing 321 and a ceiling member 324. Opposite the ceiling 324 is floor member 325. The chamber housing 321, ceiling 324 and the floor 325 are preferably made from a low density material, such as resin sand, ceramics, refractory cement, or similar materials known in the art. A generally cylindrical chamber wall 326 is adhered within and separated from the measurement head 311 by a small gap. An inlet component 327, preferably made from quartz, extends from a shallow cavity 319 in the measurement head 311 to an opening in the chamber wall. The minimum distance from the base of the cavity 319 to the outermost distal end of the inlet component 327 (i.e., the inlet opening 327a) is preferably be at least half of the diameter of the inlet opening $$\left(\text{i.e., } \frac{Diameter_{inlet}}{2}\right).$$

The inlet opening 327a is preferably closed by a steel cap 329 and the inlet component 327 preferably contains a deoxidant 328, preferably aluminum. The inlet cap 329 may or may not be covered by a small paper disk (not shown).

The internal volume of the solidification chamber 331 is defined as the volume contained within the chamber 331, between the chamber wall 326, the floor 325, and the ceiling 324 of the chamber 331. The mass of metal contained in the chamber 331 can be calculated by multiplying the chamber 331 volume by the density of the metal filling the chamber 331, less the volume displaced by the extending thermocouple element 323. Preferably, the mass ratio between the volume of the metal sampled and the mass of the chamber wall 326 is greater than 2.6 and less than 6

$$\left(\text{e.g., } 6 > \frac{M_{sample}}{M_{wall}} > 2.6\right).$$

The present invention allows for accurate bath temperatures and accurate bath carbon measurements to be made under in-blow conditions in a steelmaking converter. An added benefit of the thermal arrest chamber design according to the present invention is the rapid filling and solidification of the metal sample in the sample chamber 20, 216, 331, thereby resulting in a liquidus and bath carbon measurement in preferably less than six seconds, well below the lifetime of the signal cable 8, 208, 308.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A drop-in probe for determining phase changes by thermal analysis of a sample of a molten metal, the drop-in probe comprising:
   a measurement head including a first end which is an immersion end and an opposing second end having an end face, a body of the measurement head being formed of a first body half and a second body half configured to mate with the first body half along a parting line;
   a sample chamber arranged within at least one of the first body half and the second body half of the measurement head, the sample chamber being thermally isolated from a cooling mass of the measurement head, the sample chamber including a first thermocouple having a first hot junction enclosed within a metal wall, the metal wall having a thickness of 2.5 mm or less; and
   an inlet tube having an inlet opening of a diameter $D_{inlet}$, the inlet opening being spaced apart from the end face of the second end of the measurement head at a distance of at least $$\frac{D_{inlet}}{2},$$

wherein, when the sample chamber is filled with a sample of the molten metal, a ratio of a mass of the metal accommodated in the sample chamber to a mass of the metal wall of the sample chamber is greater than 2.6 and less than 6.

2. The drop-in probe according to claim 1, wherein in a mated configuration of the first and second body halves, a lateral axis of each body half at the immersion end is angled away from the parting line of the measurement head.

3. The drop-in probe according to claim 1, wherein the $D_{inlet}$ of the inlet opening is 15 mm or less.

4. The drop-in probe according to claim 1, further comprising a second thermocouple having a second hot junction at the immersion end of the measurement head.

5. The drop-in probe according to claim 1, wherein one of the first and second body halves includes at least one depression and wherein the other of the first and second body halves includes at least one raised ridge configured to fit within the at least one depression.

6. The drop-in probe according to claim 1, wherein the first and second body halves are made from cast iron.

7. The drop-in probe according to claim 1, wherein the sample chamber has a floor and a ceiling, both of which are constructed of a material selected from the group consisting of a resin sand, a refractory cement and a ceramic.

8. The drop-in probe according to claim 1, wherein the inlet tube is made of quartz.

9. The drop-in probe according to claim 1, further comprising an extension tube emerging from second end of the measurement head and a signal cable extending through the extension tube and exiting therefrom at an outlet opening.

10. The drop-in probe according to claim 9, wherein the extension tube is made of a material selected from the group consisting of a metal, a plastic, a rubber, a paper material and a woven material.

11. The drop-in probe according to claim 1, further comprising a cap attached to the immersion end.

12. The drop-in probe according to claim 11, wherein the cap is made of a high density polymer.

13. The drop-in probe according to claim 1, further comprising a deoxidant positioned within the inlet tube.

14. The drop-in probe according to claim 13, wherein the deoxidant is aluminum.

15. The drop-in probe according to claim 1, further comprising a cap covering the inlet opening.

16. The drop-in probe according to claim 15, wherein the cap is made of steel.

* * * * *